(12) United States Patent
Naya et al.

(10) Patent No.: US 8,213,004 B2
(45) Date of Patent: Jul. 3, 2012

(54) METHOD AND APPARATUS FOR MEASURING RAMAN SIGNALS

(75) Inventors: Masayuki Naya, Ashigara-kami-gun (JP); Yuichi Tomaru, Ashigara-kami-gun (JP); Naoki Murakami, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 251 days.

(21) Appl. No.: 12/409,056

(22) Filed: Mar. 23, 2009

(65) Prior Publication Data

US 2009/0248367 A1    Oct. 1, 2009

(30) Foreign Application Priority Data

Mar. 26, 2008  (JP) ................................. 2008-080217

(51) Int. Cl.
*G01J 3/44* (2006.01)
(52) U.S. Cl. .......... 356/301; 702/32; 702/134; 702/189; 702/190
(58) Field of Classification Search .................... 702/28, 702/32, 194
See application file for complete search history.

(56) References Cited

U.S. PATENT DOCUMENTS

| | | | | |
|---|---|---|---|---|
| 4,768,879 A * | 9/1988 | McLachlan et al. | .......... | 356/301 |
| 5,582,168 A * | 12/1996 | Samuels et al. | ............... | 600/407 |
| 5,765,948 A * | 6/1998 | Sai | ................. | 374/161 |
| 6,180,415 B1 * | 1/2001 | Schultz et al. | ................ | 436/518 |
| 6,888,629 B1 | 5/2005 | Boss et al. | | |
| 7,999,934 B2 * | 8/2011 | Naya et al. | ..................... | 356/301 |
| 2003/0135122 A1 * | 7/2003 | Bambot et al. | ................ | 600/476 |
| 2004/0130714 A1 * | 7/2004 | Gellerman et al. | ........... | 356/300 |
| 2005/0105085 A1 | 5/2005 | Naya | | |
| 2009/0273780 A1 * | 11/2009 | Tomaru et al. | ................ | 356/301 |

FOREIGN PATENT DOCUMENTS

| | | |
|---|---|---|
| JP | 2000-258346 A | 9/2000 |
| JP | 2005-172569 A | 6/2005 |

* cited by examiner

*Primary Examiner* — Drew A Dunn
*Assistant Examiner* — Mischita Henson
(74) *Attorney, Agent, or Firm* — Sughrue Mion, PLLC (57) ABSTRACT

A method of measuring Raman signals comprises: an analyte placing step of placing an analyte on a detection surface of a microstructure plate which generates an enhanced electric field when irradiated with excitation light; an irradiating step of irradiating the detection surface with the excitation light so that the enhanced electric field is generated around the detection surface and light is emitted from the analyte and the detection surface to be enhanced by the generated enhanced electric field; a Raman signal obtaining step of detecting the enhanced light to obtain a Raman signal emitted from the analyte and a background signal for use as a reference, the Raman signal and the background signal having respective intensities; and a normalizing step of normalizing the Raman signal from the analyte by dividing the intensity of the Raman signal from the analyte by the intensity of the background signal obtained as the reference.

10 Claims, 6 Drawing Sheets

METHOD AND APPARATUS FOR MEASURING RAMAN SIGNALS

The entire contents of all documents cited in this specification are incorporated herein by reference.

BACKGROUND OF THE INVENTION

The present invention relates to a method and apparatus for measuring Raman signals by radiating a detection surface on which an analyte has been placed with excitation light and, in a state where an enhanced electric field has been generated at the detection surface, detecting Raman scattered light from the analyte.

Raman spectroscopy is a technique, used for identifying substances and other purposes, in which Raman scattered light obtained by radiating a substance with single-wavelength light is spectrally analyzed to give Raman scattered light signals. Raman spectroscopy can be used to measure (e.g., identify) biosamples.

In addition, as mentioned in the method for quantitatively analyzing a substrate by Raman spectroscopy described in JP 2000-258346 A, because there is a correlation between the concentration of the substance to be assayed and the intensity of the Raman scattered light, it is possible to determine the concentration or amount of an analyte based on the intensity of the Raman scattered light.

However, Raman scattered light obtained from the substance (i.e., the analyte) is weak, making it difficult to carry out such measurement at a high sensitivity.

To address this problem, JP 2005-172569 A discloses a method which uses a microstructure plate having formed thereon a detection surface where a plurality of fine metal particles of a size capable of exciting localized plasmons are disposed, which region, when irradiated with light, forms an enhanced electric field and amplifies Raman scattered light.

By employing surface-enhanced Raman scattering (SERS), which generates an enhanced electric field on the detection surface and thereby increases the signal intensity of Raman scattered light, it is possible to detect an analyte even when, owing to a low concentration, for example, little analyte is present on the detection surface.

U.S. Pat. No. 6,888,629, which relates to a method for detecting an analyte by the SERS technique, describes a method wherein signals other than Raman scattered light from the analyte (secondary signals) are filtered from all the signals detected so as to extract Raman scattered light signals representing the analyte. The secondary signals are data that have been stored in a processor, and detection is described as being carried out by detecting the Raman scattered light in a state where the analyte is not loaded in the measurement apparatus.

SUMMARY OF THE INVENTION

In the SERS technique which enhances Raman scattered light with an enhanced electric field generated on a microstructure plate, because the degree of signal enhancement is determined by the microstructure plate, in a case that there is much structural variability in the microstructure plate, the signal variance also becomes large. That is, if the strength of the enhanced electric field differs with each microstructure plate used in measurement or if the strength of the enhanced electric field differs from one another according to positions or regions on a microstructure plate, the enhanced Raman scattered light signals also end up being variable.

When the signals are variable in this way, it is difficult to quantitatively measure the amount and concentration of the analyte.

To avoid such problems, many ways have been proposed for uniformly manufacturing microstructure plates. Unfortunately, because it is impossible to manufacture perfectly uniform microstructure plates, the uniformity of signal intensity has been limited.

The SERS technique is able to enhance weak Raman scattered light, and can thus be used to monitor Raman scattered light from an analyte at high sensitivity. However, not only Raman scattered light from the analyte, but also light such as Raman scattered light and fluorescent light from the background (i.e., areas within a detection surface other than a region where the analyte was placed) are also enhanced. As a result, the signal variance between microstructure plates becomes larger.

Up until now, as with the method described in U.S. Pat. No. 6,888,629, to monitor Raman scattered light from an analyte at a high sensitivity, background signals have been removed from the total signals detected. However, it has not been possible with this approach to correct for the variability in signal strength between microstructure plates.

Also, the method described in U.S. Pat. No. 6,888,629 is a method for detecting only the Raman signals from the analyte; the quantitative determination of the analyte is not described. Moreover, even in cases where data stored in a processor is used, because the detected values vary from one microstructure plate to another, quantitative determination of the analyte is likewise difficult.

Even though Raman signals originating from substances other than the analyte can be filtered out, the degree of signal enhancement due to the enhanced electric field cannot be detected. It is difficult to quantitatively measure the analyte in this regard as well.

In addition, a method has also been proposed for normalizing Raman signals by mixing the analyte with a reference substance having a known Raman activity and comparing the signals with each other.

However, in this method, the affinity between the analyte and the reference substance must be taken into account. For example, when the analyte and the reference substance differ from each other in facility of bonding to the microstructure plate, the substance to bond more readily will preferentially adsorb to the surface of the microstructure plate and the substance to bond less readily will be pushed away, thus making it impossible to hold down the signal strength variability.

It is therefore an object of the present invention to provide a method of measuring Raman signals which is able to reduce signal strength variability between microstructure plates. Another object of the invention is to provide an apparatus for measuring Raman signals which similarly is able to reduce signal strength variability between microstructure plates.

A method of measuring Raman signals according to the present invention comprises: an analyte placing step of placing an analyte on a detection surface of a microstructure plate which generates an enhanced electric field when irradiated with excitation light; an irradiating step of irradiating the detection surface with the excitation light so that the enhanced electric field is generated around the detection surface and light is emitted from the analyte and the detection surface to be enhanced by the generated enhanced electric field; a Raman signal obtaining step of detecting the enhanced light to obtain a Raman signal emitted from the analyte and a background signal for use as a reference, the Raman signal and the background signal having respective intensities; and a normalizing step of normalizing the Raman signal from the analyte by dividing the intensity of the Raman signal from the analyte by the intensity of the background signal obtained as the reference.

An apparatus for measuring Raman signals according to the present invention comprises: a microstructure plate on which is formed a detection surface that generates an enhanced electric field when irradiated with excitation light, for placing an analyte on the detection surface; excitation light radiating means that irradiates the detection surface of the microstructure plate with the excitation light so that the enhanced electric field is generated around the detection surface and light is emitted from the analyte and the detection surface to be enhanced by the generated enhanced electric field; detection means that detects the enhanced light to obtain a Raman signal emitted from the analyte and a background signal for use as a reference, the Raman signal and the background signal having respective intensities; and normalization processing means that normalizes the Raman signal from the analyte by dividing the intensity of the Raman signal from the analyte by the intensity of the background signal obtained as the reference.

DETAILED DESCRIPTION OF THE INVENTION

The method and apparatus for measuring Raman signals of the present invention are described in detail below based on the embodiments shown in the accompanying diagrams.

Figure 1:
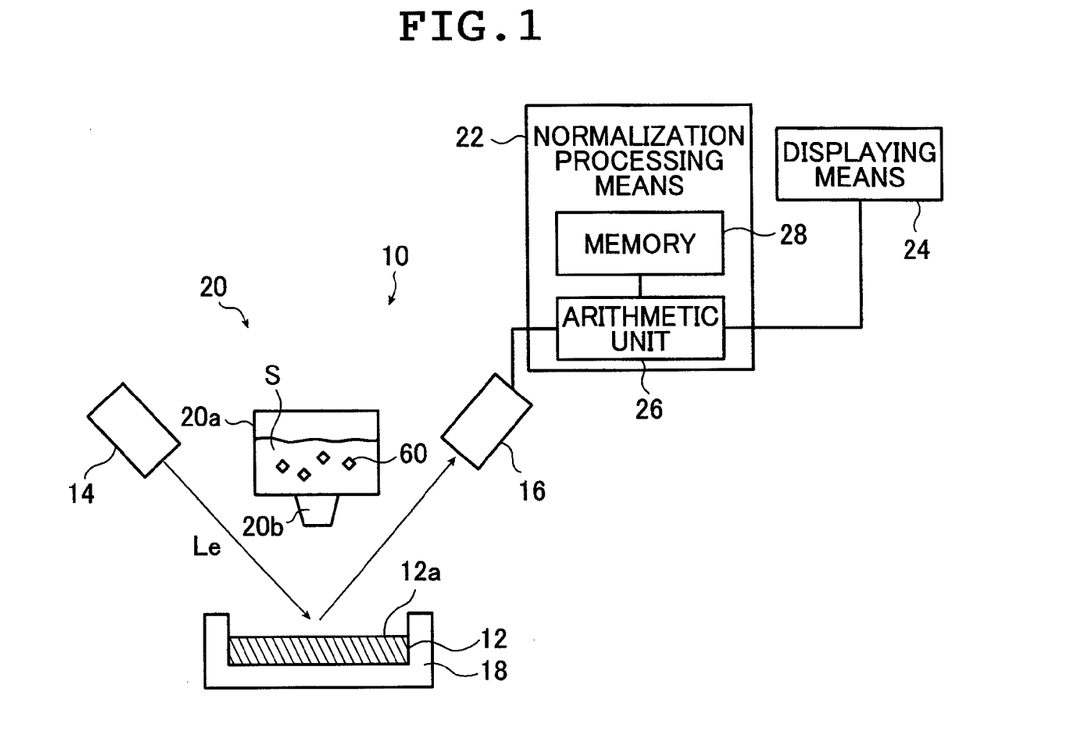
FIG. 1 is a block diagram which schematically shows the configuration of an embodiment of an apparatus for measuring Raman signals of the invention.
Figure 2:
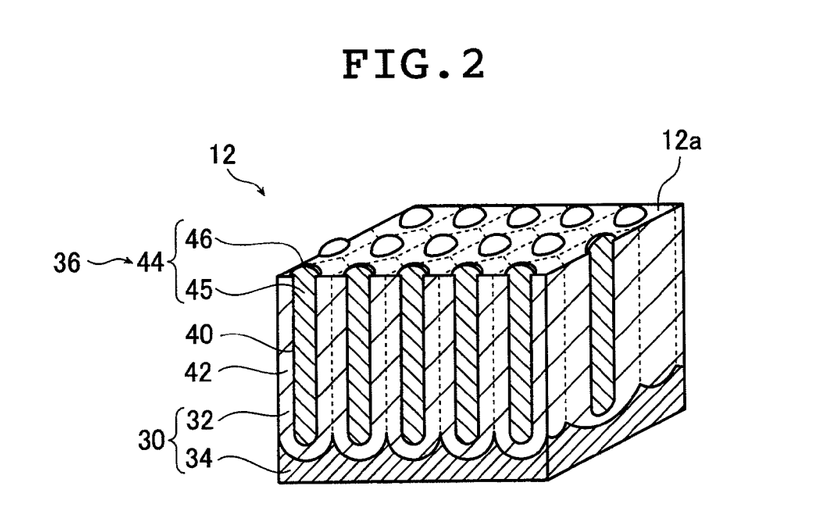
FIG. 2 is a simplified perspective view showing a microstructure plate used in the apparatus for measuring Raman signals shown in FIG. 1.

FIG. 1 is a front view which schematically shows the configuration of a Raman signal measuring apparatus 10 according to an embodiment of the invention. FIG. 2 is a simplified, perspective view of a microstructure plate 12 used in the Raman signal measuring apparatus 10 shown in FIG. 1.

Referring to FIG. 1, the Raman signal measuring apparatus 10 has the microstructure plate 12, an excitation light radiating means 14 for radiating the microstructure plate 12 with excitation light, a detection means 16 for enhancing Raman scattered light generated from a detection surface 12a and the proximity thereof, detecting the enhanced Raman scattered light and obtaining a Raman signal emitted from an analyte 60 and a background signal for use as a reference, a chip support means 18 for supporting the microstructure plate 12, a liquid sample dropping means 20 which drops a liquid sample S containing the analyte 60 onto the microstructure plate 12, a normalization processing means 22 which normalizes the intensity of a Raman signal from the analyte 60 detected by the detection means 16, and a displaying means 24 which displays the results of computations by the normalization processing means 22.

Although not shown, the Raman signal measuring apparatus 10 also has a housing which covers the respective elements, including the microstructure plate 12, the excitation light radiating means 14 and the detection means 16; various optical members such as filters for removing stray light generated at the interior of the Raman signal measuring apparatus 10; and various members essential to the Raman signal measuring apparatus 10, such as a controller for controlling operation of the Raman signal measuring apparatus 10.

As illustrated in FIG. 2, the microstructure plate 12 comprises a substrate 30 including a dielectric base 32 and an electric conductor 34 disposed on one surface of the dielectric base 32 and metallic members 36 disposed on the side of the dielectric base 32 opposite from the electric conductor 34.

The substrate 30 comprises the dielectric base 32 formed of a metallic oxide ($Al_2O_3$) and the electric conductor 34 disposed on the one surface of the dielectric base 32 and formed of a non-anodized metal (Al). The dielectric base 32 and the electric conductor 34 are formed integrally.

The dielectric base 32 has micropores 40 each having the shape of a substantially straight tubing that extends from the surface opposite from the electric conductor 34 toward the surface closer to the electric conductor 34.

Each micropore 40 is formed through the surface of the dielectric base 32 so as to have an opening at one end thereof opposite from the electric conductor 34, with the other end closer to the electric conductor 34 closing short of the opposite surface of the dielectric base 32. In other words, the micropores 40 do not reach the electric conductor 34. The micropores 40 each have a diameter smaller than the wavelength of the excitation light and are arranged regularly at a pitch smaller than the wavelength of the excitation light.

When the excitation light used is a visible light, the micropores 40 are preferably arranged at a pitch of 200 nm or less.

The metallic members 36 are formed of rods 44 each having a filler portion 45 filling the inside of each micropore 40 of the dielectric base 32 and a projection 46 (bulge) which has an outer diameter greater than that of the filler portion 45 and has dimensions permitting excitation of localized plasmons. The material for forming the metallic members 36 may be selected from various metals capable of exciting localized plasmons and include, for example, Au, Ag, Cu, Al, Pt, Ni, Ti, and an alloyed metal thereof. Further, the metallic members 36 may also contain two or more of these metals. To obtain a further enhanced field effect, the metallic members 36 are more preferably formed using Au or Ag.

The plurality of rods 44 in the metallic member 36 are preferably arranged in such a way that the distance separating a projection 46 from the neighboring projections 46 is not more than several tens of nanometers.

By setting the interval between the projections 46 to several tens of nanometers or less, at the time of irradiation with excitation light, a highly enhanced electric field can be formed in regions where the projections 46 are in close proximity to each other. Regions where a highly enhanced electric field is formed at an interval between projections 46 of several tens of nanometers or less are called "hot spots."

In the microstructure plate 12 having the above-described construction, a surface on which the projections 46 of the plurality of rods 44 in the metallic member 36 are disposed is where the liquid sample S comes into contact with the microstructure plate 12, and is referred to herein as a detection surface 12a.

Next, a process for manufacturing the microstructure plate 12 is described.

Figure 3A:
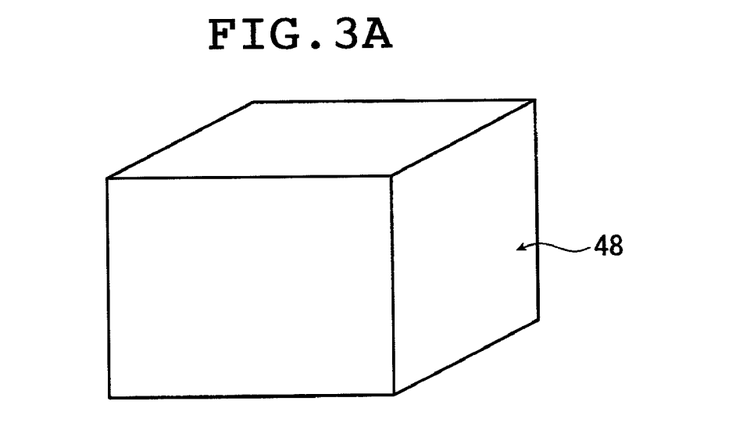
FIGS. 3A to 3C illustrate a process for manufacturing the microstructure plate.
Figure 3B:
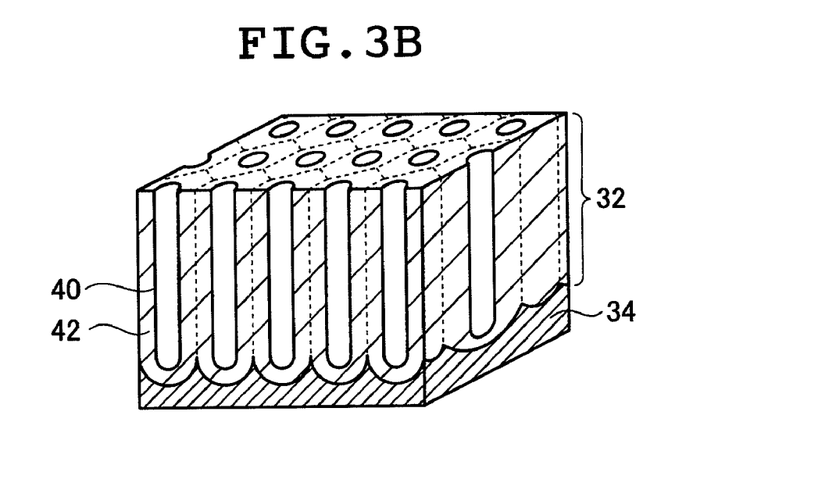
Figure 3C:
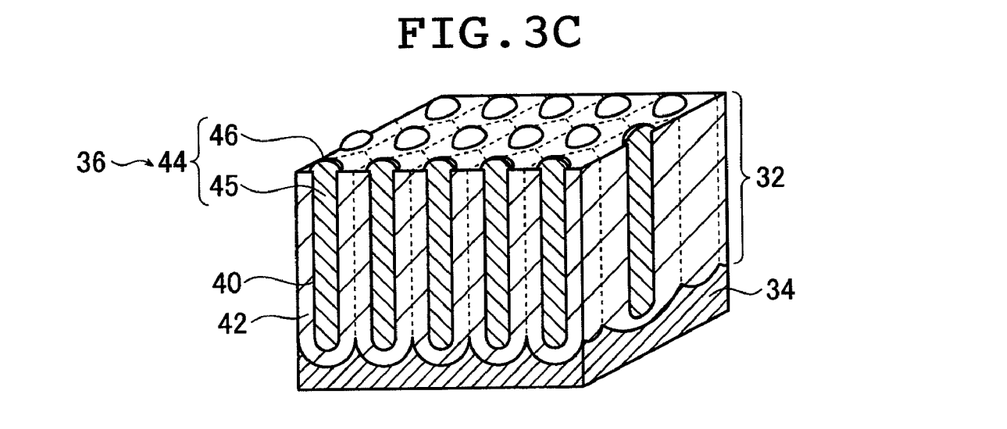

FIGS. 3A to 3C illustrate a process for manufacturing the microstructure plate 12.

First, the method of producing the microstructure plate 12 used for the specimen detecting device 10 will be described.

First, a metallic body 48 to be anodized having the shape of a rectangular solid as illustrated in FIG. 3A is anodized. Specifically, the metallic body 48 to be anodized is submerged in an electrolytic solution as an anode together with a cathode, whereupon an electric voltage is applied between the anode and the cathode to achieve anodization.

The cathode may be formed, for example, of carbon or aluminum. The electrolytic solution is not limited specifically; preferably used is an acid electrolytic solution containing at least one of sulfuric acid, phosphoric acid, chromic acid, oxalic acid, sulfamic acid, benzenesulfonic acid and amidosulfonic acid.

Although the metallic body 48 to be anodized has the shape of a rectangular solid in this embodiment, the shape is not limited thereto and may vary. Further, one may use a configuration comprising a support member on which, for example, a layer of the metallic body 48 to be anodized is formed.

Anodization of the metallic body 48 causes oxidation to take place as illustrated in FIG. 3B from the surface of the metallic body 48 in a direction substantially vertical to that surface, producing a metallic oxide ($Al_2O_3$), which is used as the dielectric base 32. The metallic oxide produced by anodization or the dielectric base 32 has a structure wherein numerous minute columns 42 each having a substantially hexagonal shape in planar view are arranged leaving no space between them.

The minute columns 42 each have a round bottom end and a micropore 40 positioned substantially at its center and extending straight from the top surface in the depth direction, i.e., in the direction of the axis of each minute column 42. For the structure of a metallic oxide produced by anodization, reference may be had, for example, to "Production of Mesoporous Alumina using Anodizing Method and Applications Thereof as Functional Material" by Hideki Masuda, page 34, Zairyo Gijutsu (Material Technology), Vol. 15, No. 10, 1997.

An example of preferred anodization conditions for producing a metal oxide having a regularly arrayed structure includes an electrolytic solution having a concentration of 0.5 M, a liquid temperature in the range of 14° C. to 16° C., and an applied electric voltage of 40 V to 40 V+/−0.5 V among other conditions when using oxalic acid as an electrolytic solution. The micropores 40 produced under these conditions each have, for example, a diameter of about 30 nm and are arranged at a pitch of about 100 nm.

Next, the micropores 40 of the dielectric base 32 are electroplated to form the rods 44 each having the filler portion 45 and the projection 46 as illustrated in FIG. 3C.

In the electroplating, the electric conductor 34 acts as an electrode, causing a metal to be deposited preferentially from the bottoms of the micropores 40 where the electric field is stronger. Continuous electroplating causes the micropores 40 to be filled with a metal, forming the filler portions 45 of the rods 44. Electroplating further continued after the formation of the filler portions 45 causes the metal to overflow from the micropores 40. However, the electric field near the micropores 40 is so strong that the metal continues to be deposited around each micropore 40 until the metal is deposited above the filler portions 45 so as to project from the surface of the dielectric base 32, thus forming the projections 46 having a diameter greater than that of the filler portions 45.

Since the microstructure plate 12 according to the above embodiment is produced using anodization, it is easy to produce the microstructure plate 12 where the micropores 40 of the dielectric base 32 and the projections 46 of the metallic members 36 are arranged substantially regularly. Alternatively, the micropores may be arranged randomly.

Although only Al is cited as a major component of the metallic body 48 to be anodized that is used to produce the dielectric base 32 in the above embodiment, any metal may be used, provided that it is anodizable and forms a metallic oxide. Other metals than Al that may be used include Ti, Ta, Hf, Zr, Si, In, and Zn. The metallic body 48 to be anodized may contain two or more kinds of anodizable metals.

The microstructure plate 12 is thus manufactured as described above.

The excitation light radiating means 14 comprises a light source such as a laser light source, and a light guiding system which guides light of a specific wavelength (excitation light) Le emitted by the light source. The excitation light radiating means 14 emits the excitation light Le, and irradiates the detection surface 12a of the microstructure plate 12 with the emitted excitation light Le.

The detection means (i.e., spectrally analyzing means) 16 is composed of a spectral detector, and is situated at an incident position for scattered light generated at the detection surface of the microstructure plate 12 when the microstructure plate 12 is irradiated with excitation light from the excitation light radiating means 14.

The detection means 16 spectrally analyzes light generated at the detection surface 12a of the microstructure plate 12, and detects a Raman scattered light signal (Raman signal) from the analyte. Concurrent with the Raman signal from the analyte, the detection means 16 also detects a signal (background signal) such as Raman scattered light or fluorescence generated when the microstructure plate 12 is irradiated with the excitation light Le.

Here, the background signal is a signal due to light from the detection surface 12a of the microstructure plate 12 and from a substance other than the analyte 60 which may be present on the detection surface 12a (these are referred to collectively in the present specification as the "background"). Such a background signal may be basically regarded as a Raman scattered light or fluorescence signal from the detection surface proper of the microstructure plate 12, and is not subject to any particular limitation.

Illustrative examples of the detected light for use as a reference which is detected so as to obtain the above-described background signal include the Raman scattered light, fluorescence, reflected light, absorbed light and transmitted light generated when the microstructure plate 12 is irradiated with the excitation light Le. Raman scattered light or fluorescence from the detection surface 12a proper of the microstructure plate 12 is preferred.

The chip support means 18 is a seating or the like and holds the microstructure plate 12 in a given position by supporting the microstructure plate 12 from the side thereof bearing the electric conductor 34. The chip support means 18 comprises an enclosure for covering the outer periphery of the lateral sides of the microstructure plate 12 to prevent a liquid from spilling out from the surface of the microstructure plate 12 when the liquid is dropped onto the microstructure plate 12.

The liquid sample dropping means 20 comprises a reservoir 20a for storing a liquid sample S containing the analyte 60 and a dropping mechanism 20b for dropping the liquid sample S stored in the reservoir 20a onto the microstructure plate 12. The liquid sample dropping means 20 is disposed opposite the detection surface of the microstructure plate 12.

The reservoir 20a is a vessel which stores the liquid sample S containing the analyte 60. This reservoir 20a stores a fixed amount of the liquid sample S.

When the analyte 60 is a substance which is not present in a liquid, the liquid sample S may be prepared by dispersing the analyte 60 in a solvent. Various solvents may be used as the solvent for dispersing the analyte. Illustrative examples include water, ethanol, and aqueous solutions in which various substances have been dissolved (e.g., aqueous solutions of citric acid). In the present embodiment, it is preferable to use a volatile solvent as the solvent. The use of ethanol is especially preferred.

The dropping mechanism 20b drops onto the microstructure plate 12 a fixed amount of the liquid sample S stored in the reservoir 20a. A dropper or the like may be used as the dropping mechanism 20b.

The liquid sample dropping means 20 configured as described above uses the dropping mechanism 20b to drop onto the detection surface 12a of the microstructure plate 12 a predetermined amount of the liquid sample S stored in the reservoir 20a.

The normalization processing means 22 has an arithmetic unit 26 which arithmetically processes data received from the detection means 16, and a memory 28 which stores, for example, data received from the detection means 16 and the results of computations by the arithmetic unit 26. The normalization processing means 22 normalizes the analyte Raman signal detected by the detection means 16, and computes the amount or concentration of the analyte 60.

The displaying means 24 is a device which displays images, such as a liquid crystal display. In the present embodiment, the displaying means 24 displays information such as computation results received from the normalization processing means 22, and Raman signals.

The Raman signal measuring apparatus 10 is basically configured as described above.

A more detailed description of the inventive method of measuring Raman signals is given below by describing the operation of the Raman signal measuring apparatus 10.

Figure 4A:
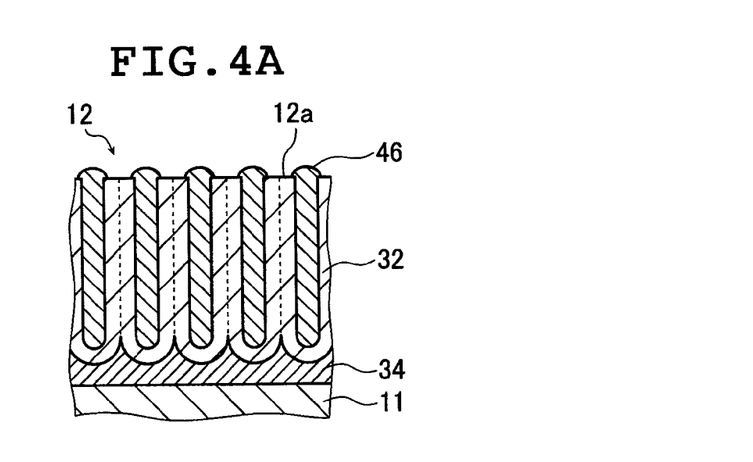
FIGS. 4A to 4C illustrate in stepwise an embodiment of the Raman signal measurement method of the invention.
Figure 4B:
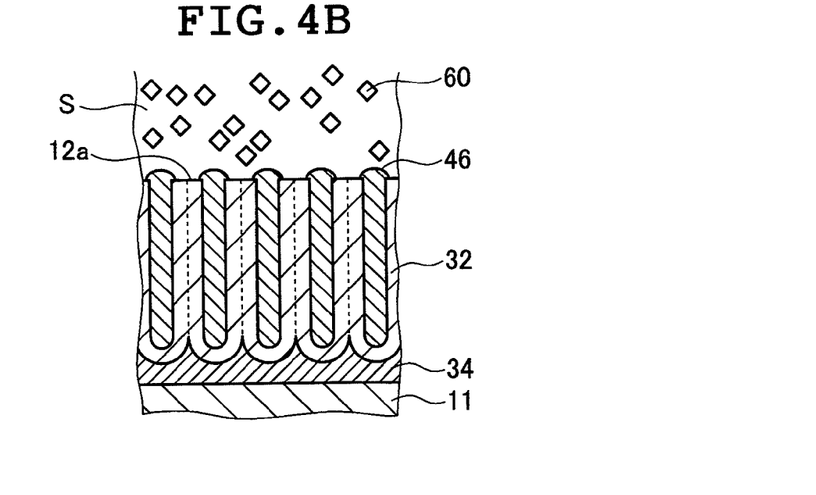
Figure 4C:
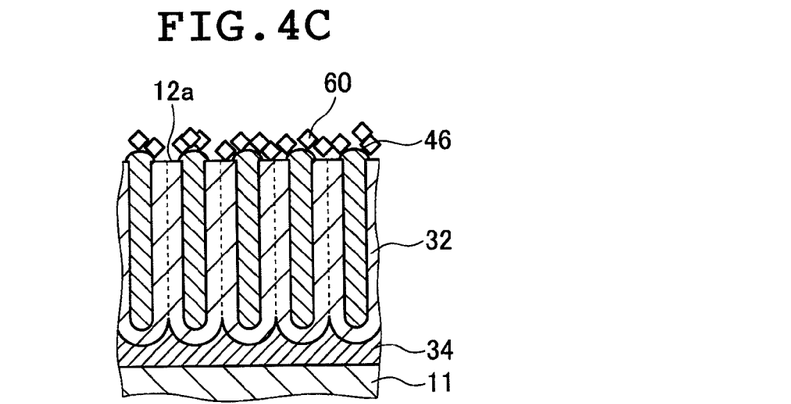

FIGS. 4A to 4C illustrate an embodiment of the inventive method of measuring Raman signals.

First, the microstructure plate 12 is placed at a predetermined position on the chip support means 18, and is secured at the predetermined position.

In addition, a liquid sample S containing an analyte 60 as the assay target is placed in the reservoir 20a.

Next, a predetermined amount of the liquid sample S is dropped onto the detection surface 12a of a microstructure plate 12 like that shown in FIG. 4A by the liquid sample dropping means 20.

As a result, the liquid sample S containing the analyte 60 collects on and becomes held by the microstructure plate 12 and the chip support means 18 and, as shown in FIG. 4B, enters into a state of contact with the detection surface 12a of the microstructure plate 12.

Next, the detection surface 12a is dried to remove the liquid component (solvent) of the liquid sample S which is in contact therewith. As shown in FIG. 4C, this results in the analyte 60 adhering to the detection surface 12a of the microstructure plate 12 around the projections 46.

Next, excitation light Le is emitted from the excitation light radiating means 14, and made to illuminate the detection surface 12a to which the analyte 60 has been attached.

The detection surface 12a of the microstructure plate 12, when irradiated with the light emitted by the excitation light radiating means 14, generates localized plasmons at the surfaces of the projections 46 on the metallic member 36, resulting in the formation of an enhanced electric field around the detection surface 12a.

Moreover, on the microstructure plate 12, localized plasmon resonance which enhances the electric field is effectively generated at the surfaces of the projections 46 on the metallic member 36. Localized plasmon resonance is the phenomenon where metal free electrons experiencing locally collective movement due to localized plasmons oscillate in resonance with the electric field of light, enhancing the electric field. At the projections 46 (bulges) which give the microstructure plate 12 an irregular surface shape, in regions where the wavelength of the incident light matches the size of the surface irregularities, the free electrons of the projections 46 oscillate in resonance with the electric field of the light. As a result, the incident light is very efficiently altered by the electric field, further enhancing the electric field around the projections 46.

In this way, an electric field enhancing effect can be obtained at the detection surface 12a of the microstructure plate 12, resulting in the formation of an enhanced electric field. Because the microstructure plate 12 is able to further enhance the electric field, it is advantageous to design and adjust the wavelength of the excitation light and the size of the projections 46 so that localized plasmon resonance arises at the projections 46. At the very least, localized plasmons should be generated at the projections 46.

The analyte 60 on the detection surface 12a generates Raman scattered light from the impingement thereon of excitation light of a specific wavelength.

The background (the detection surface 12a of the microstructure plate 12, and substances other than the analyte 60 which may be present on the detection surface 12a) also generates Raman scattered light from the impingement thereon of excitation light of a specific wavelength. In some cases, such as when the metallic member 44 of the microstructure plate 12 is made of Au, the microstructure plate 12 sometimes generates fluorescence upon the impingement of excitation light of a specific wavelength.

Light such as Raman scattered light and fluorescence generated from the analyte 60 and the background is enhanced by the enhanced electric field which has been generated due to localized plasmons.

The Raman scattered light signal emitted by the analyte 60 varies depending on the type of analyte detected.

The detection means 16 spectrally analyzes light from the detection surface 12a of the microstructure plate 12, and detects a Raman signal from the analyte 60. Simultaneous with the Raman signal from the analyte 60, the detection means 16 also detects a background signal for use as a reference.

The detected signals are then sent to the normalization processing means 22.

Figure 5:
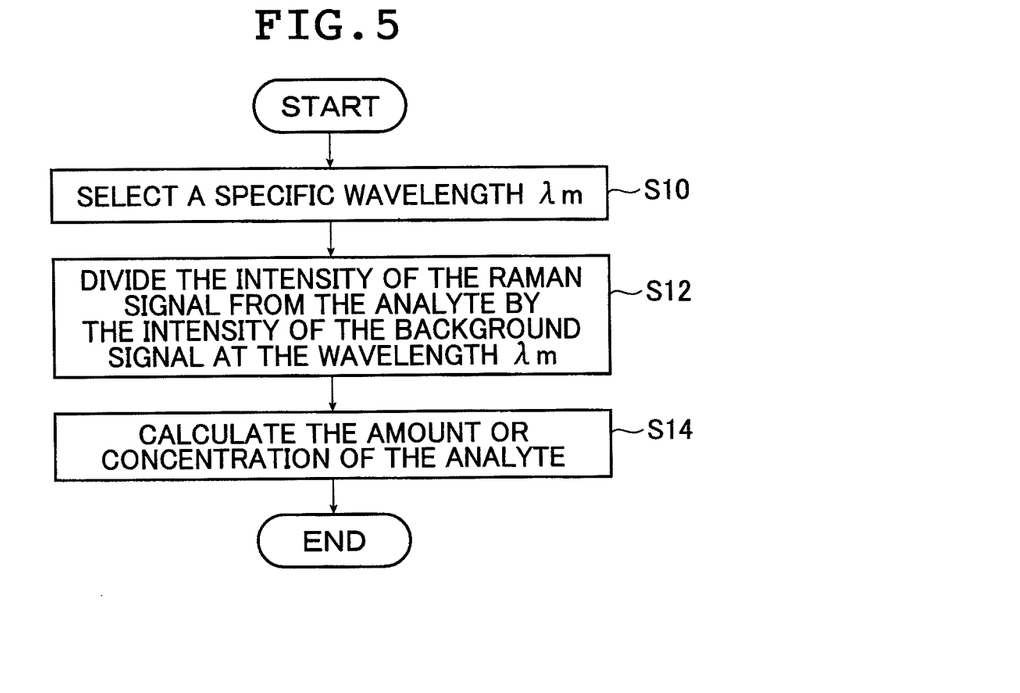
FIG. 5 is a flow diagram showing an embodiment of the steps for computing the amount or concentration of an analyte by a normalization processing means.

Here, FIG. 5 is a flow diagram showing an embodiment of the steps for computing the amount or concentration of the analyte 60 by the normalization processing means 22.

First, a specific wavelength $\lambda_m$ is selected (Step S10). Specifically, a wavelength differing from the wavelength $\lambda_r$ of the Raman signal from the detected analyte 60 is selected as the wavelength $\lambda_m$. Preferably, a wavelength which differs from the half-value width of the Raman signal from the analyte 60 is selected.

Although not shown in FIG. 5, in cases where an unknown substance is used as the analyte 60, before selecting the above wavelength $\lambda_m$ (Step S10), it is preferable to identify the analyte 60 by comparing the detected signal with the Raman signals for various substances that are stored in the memory 28, and specify the wavelength $\lambda_r$ of the Raman signal from the analyte 60. This step may be omitted when a known substance is used as the analyte 60.

Next, the intensity of the Raman signal from the analyte 60 is divided by the intensity of the background signal at the specific wavelength $\lambda_m$ (Step S12). In this way, the Raman signal from the analyte 60 is normalized.

In the next step, the amount or concentration of the analyte 60 is computed based on the normalized Raman signal (Step S14). The concentration can be calculated by taking into account the amount of the liquid sample S dropped onto the microstructure plate by the liquid sample dropping means 20.

Figure 6:
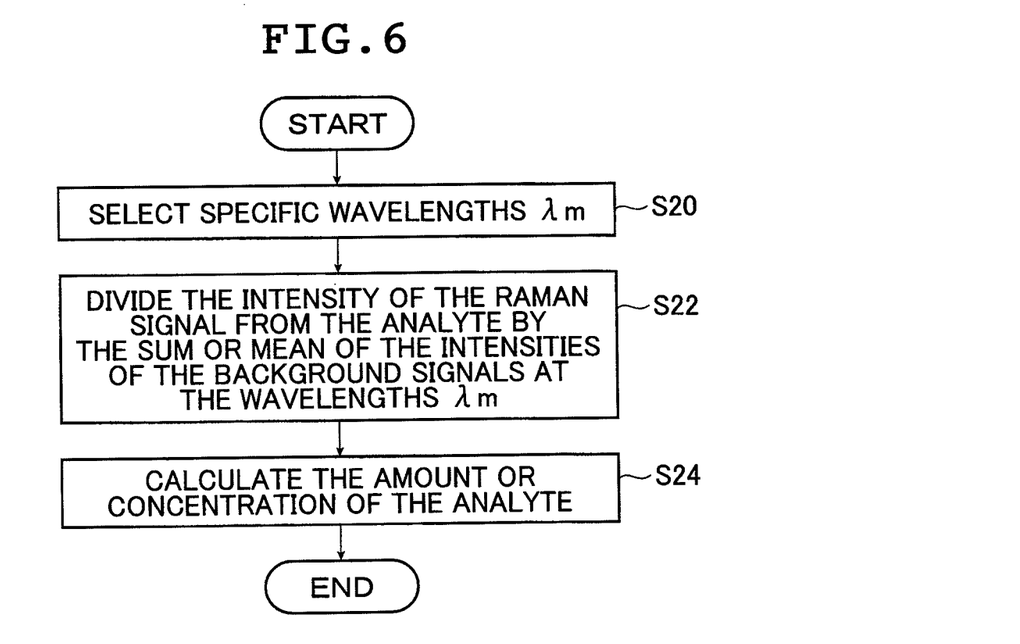
FIG. 6 is a flow diagram showing another embodiment of the steps for computing the amount or concentration of an analyte by a normalization processing means.

FIG. 6 is a flow diagram showing another embodiment of the steps for computing the amount or concentration of the analyte 60 by the normalization processing means 22.

In this embodiment, first a plurality of specific wavelengths $\lambda_m$ are selected (Step S20). The wavelengths $\lambda_m$ may be selected under the same criteria as the wavelength $\lambda_m$ in the embodiment shown in FIG. 5, although a plurality of mutually differing wavelengths $\lambda_m$ are selected in the present embodiment. For example, mutually differing wavelengths $\lambda_1, \lambda_2, \ldots, \lambda_n$ are selected as the wavelengths $\lambda_m$ from among wavelengths which differ from the wavelength $\lambda_r$ of the Raman signal from the detected analyte 60.

The number of selected wavelengths $\lambda_m$ should be two or more.

As in the embodiment shown in FIG. 5, when an unknown substance is used as the analyte 60, before the step of selecting the wavelengths $\lambda_m$ (Step S20), it is preferable to identify the analyte 60 by comparing the Raman signal from to the analyte 60 with the Raman signals of various substances stored in the memory 28, and specify the wavelength $\lambda_r$ of the Raman signal from the analyte 60.

Next, the sum or the mean of the intensities of the background signals at each of the selected wavelengths $\lambda_1$ mentioned above is determined, and the intensity of the Raman signal from the analyte 60 is divided by the resulting value (Step S22). In this way, the Raman signal from the analyte 60 is normalized.

In the next step, the amount or concentration of the analyte 60 is computed based on the normalized Raman signal (Step S24). The concentration can be calculated by taking into account the amount of the liquid sample S dropped onto the microstructure plate by the liquid sample dropping means 20.

After the amount or concentration of the analyte 60 has been calculated as explained above, the type of analyte 60 and the amount or concentration of analyte determined by the normalization processing means 22 are displayed using the displaying means 24.

The Raman signal measuring apparatus 10 thus identifies the analyte 60 and calculates the amount and concentration of the analyte 60 in the above-described way.

As explained above, the Raman signal measuring apparatus 10 normalizes the Raman signal from the analyte 60 by dividing the intensity of the Raman signal from the analyte 60 by either the intensity of the background signal at a specific wavelength $\lambda_m$ or by the sum or mean of the intensities of background signals at a plurality of wavelengths $\lambda_m$, and is able in this way to reduce the variability in signal strength between microstructure plates 12. Also, because there is no need to use a reference substance to normalize the Raman signal, the signal strength variability can be further reduced without having to take into account the affinity between the analyte 60 and such a reference substance.

It is possible in this way to quantitatively determine an analyte 60 to a high accuracy, even when there is some variability in the projections 46 that are formed on the detection surface 12a of the microstructure plate 12, the enhanced electric field which forms at the detection surface 12a is non-uniform from one microstructure plate 12 to another, and the degree of enhancement in the Raman scattered light by SERS is non-uniform.

Moreover, the analyte 60 can be quantitatively detected to a high accuracy even when the enhanced electric field at the detection surface 12a of the microstructure plate 12 is non-uniform. As a result, it is possible to use even a microstructure plate 12 in which the enhanced electric field generated at the detection surface 12a is non-uniform, i.e., a microstructure plate 12 which generates an enhanced electric field of varying strength. What this means is that the allowable range in microstructure plates 12 suitable for use can be increased, enabling a higher yield to be achieved and production costs to be reduced.

In the Raman signal measuring apparatus 10 of the invention, it is preferable to attach a specific binder to the projections 46 on the microstructure plate 12.

By disposing a specific binder at the projections 46 of the microstructure plate 12, bonding can be induced between the projections 46 of the microstructure plate 12 and a specific analyte 60 (i.e., an analyte 60 having the property of bonding with the specific binder).

Substances such as the following may be used as the specific binder.

When the analyte 60 is of at least one type selected from the group consisting of proteins, peptides and amino acids, surface modifying groups having an electrical charge opposite to that of the analyte 60 may be used as a specific binder which tonically bonds with the analyte 60. Illustrative examples include such surface modifying groups as carboxyl groups, sulfonic acid groups, phosphoric acid groups, amino groups, quaternary ammonium groups, imidazole groups, guanidinium groups and derivative groups thereof. The projections 46 may have two or more types of such surface modifying groups thereon.

Alternatively, when the analyte 60 is of at least one type selected from the group consisting of proteins, peptides and amino acids, illustrative examples of specific binders which covalently bond with the analyte 60 include such surface modifying groups as reactive ester groups (e.g., N-hydroxysuccinimidyl ester), carbodiimide groups, 1-hydroxybenzotriazole groups, hydrazide groups, sulfanyl groups, reactive disulfide groups, maleimide groups, aldehyde groups, epoxy groups, (meth)acrylate groups, hydroxyl groups, isocyanate groups, isothiocyanate groups and derivative groups thereof. The projections 46 may have two or more types of such surface modifying groups thereon.

Of the above-mentioned surface modifying groups, the use of, for example, a reactive ester group, a hydrazide group, a sulfanyl group or a reactive disulfide group as the specific binder is preferred.

As used herein, the term "reactive" means to have reactivity with the analyte 60.

It is especially preferable to attach to the projections 46 both a specific binder which ionically bonds with the analyte 60 and a specific binder which covalently bonds with the analyte 60.

In this case, the specific binder which ionically bonds with the analyte 60 and the specific binder which covalently bonds with the analyte 60 may be attached to the projections at the same time or sequentially. No particular limitation is imposed on the surface modifying positions of these specific binders; these specific binders may be bonded to each other, or may be bonded to the projections 46 independent of each other.

It is also especially preferable to attach to the projections 46 a specific binder which ionically bonds with the analyte 60, and to activate this specific binder with a specific binder which covalently bonds with the analyte 60.

For example, it is preferable to first introduce onto the projections 46 carboxyl groups which ionically bond with the analyte 60, then activate the carboxyl groups by derivation to the form of functional groups which covalently bond with the analyte 60 (e.g., reactive ester groups, hydrazide groups, sulfanyl groups and reactive disulfide groups).

Because the specific binder which ionically bonds with the analyte 60 and the specific binder which covalently bonds with the analyte 60 are mutually adjacent, each single analyte 60 can be made to strongly adsorb to the surfaces of the projections 46 with both ionic bonds and covalent bonds.

Illustrative examples of specific binders having both a surface modifying group which ionically bonds with the analyte 60 and a surface modifying group which covalently bonds with the analyte 60 include molecules which form a self-organizing film, such as 4,4-dithiodibutyric acid (DDA), 10-carboxy-1-decanethiol, 11-amino-1-undecanethiol, 7-carboxy-1-heptanethiol, 16-mercaptohexadecanoic acid and 11,11'-thiodiundeanoic acid; hydrogels such as agarose, dextran, carrageenan, alginic acid, starch and cellulose, as well as derivatives thereof (e.g., carboxymethyl derivatives); and water-swellable organic polymers such as polyvinyl alcohol, polyacrylic acid, polyacrylamide and polyethylene glycol.

For example, when the analyte 60 is adenine, preferred use can be made of, for example, 4,4-dithiodibutyric acid (DDA) or carboxymethyl dextran (CMD) as the specific binder having both a surface modifying group which ionically bonds with the analyte 60 and a surface modifying group which covalently bonds with the analyte 60.

Any of various means may be employed to dry the detection surface 12a of the microstructure plate 12 after the liquid sample S has been brought into contact with the detection surface 12a. That is, after the liquid sample S has been dropped onto the detection surface 12a of the microstructure plate 12, the detection surface 12a may be air-dried by allowing a given period of time to elapse or a heating mechanism which heats the detection surface 12a may be provided and the solvent actively evaporated.

In the Raman signal measuring apparatus 10 of the invention, it is not always necessary to dry the detection surface 12a at the time of Raman signal detection. The Raman signal may be detected with the detection surface 12a in a wet state; i.e., in a state where the solvent component of the liquid sample S is in contact with the detection surface 12a.

Particularly in cases where, in a dried state, the analyte 60 reacts, becoming a different substance, it is preferable to detect the Raman signal in a state where the solvent of the liquid sample S is in contact with the detection surface 12a.

The shape of the microstructure plate is not limited to that of the microstructure plate 12; the microstructure plate may have various other shapes, provided that the microstructure plate has projections formed on the substrate thereof each having dimensions permitting excitation of localized plasmon.

Figure 7A:
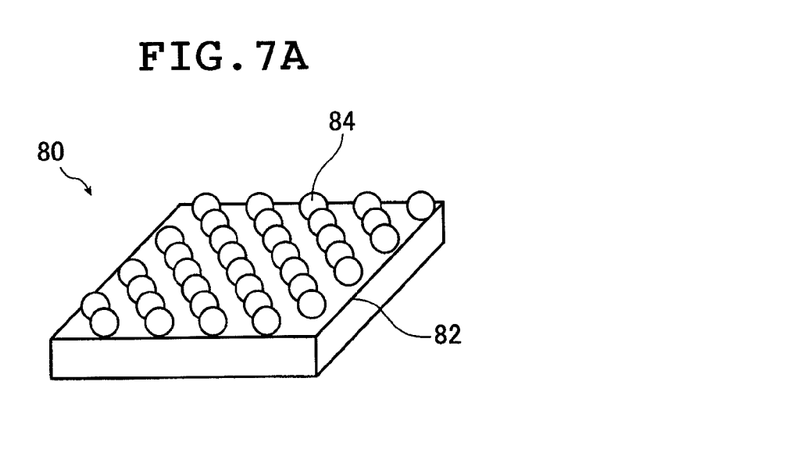
FIGS. 7A and 7B are a simplified perspective view and a partial top view showing another embodiment of a microstructure plate, respectively.
Figure 7B:
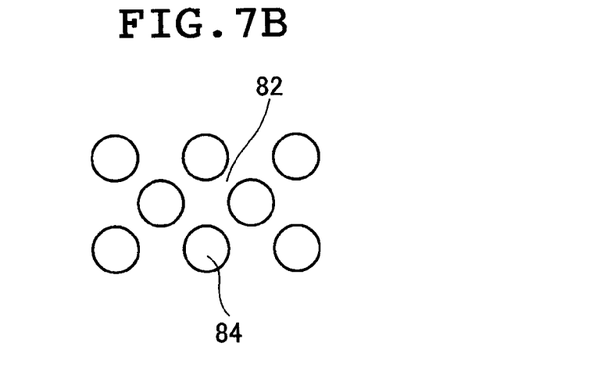

FIG. 7A is a perspective view illustrating a schematic configuration of another example of the microstructure plate; FIG. 7B is a top plan view of FIG. 7A.

A microstructure plate 80 illustrated in FIGS. 7A and 7B comprises a substrate 82 and numerous metallic particles 84 disposed on the substrate 82.

The substrate 82 is a base material in the form of a plate. The substrate 82 may be formed of a material capable of supporting the metallic particles 84 in an electrically insulated state. The material thereof is exemplified by silicon, glass, yttrium-stabilized zirconia (YSZ), sapphire, and silicon carbide.

The numerous metallic particles 84 are each of dimensions permitting excitation of localized plasmons and held in position such that they are spread on one surface of the substrate 82.

The metallic particles 84 may be formed of any of the metals cited above for the metallic members 36. The shape of the metallic particles is not limited specifically; it may be a sphere or a rectangular solid.

The microstructure plate 80 having such a configuration also generates localized plasmons around the metallic particles 84 and creates an enhanced electric field when the detection surface on which the metallic particles 84 are disposed is irradiated by the excitation light.

Figure 8:
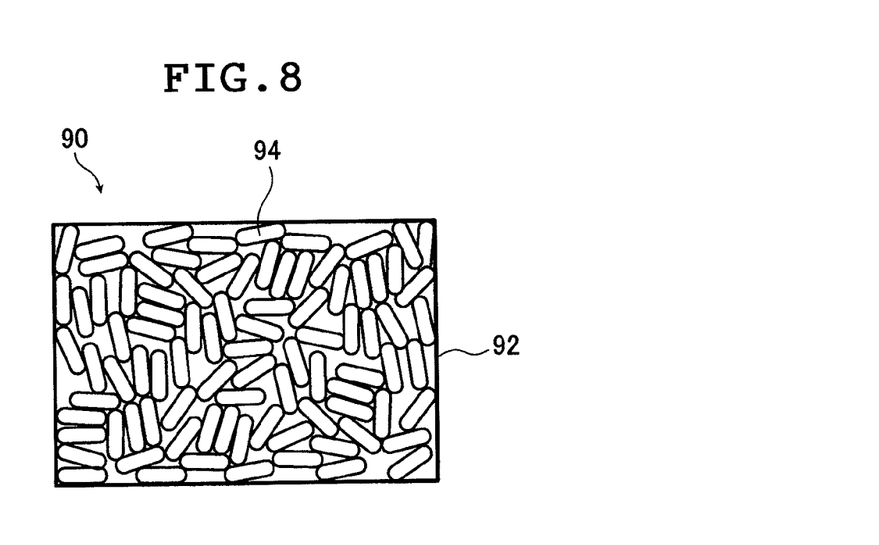
FIG. 8 is a simplified top view showing yet another embodiment of a microstructure plate.

FIG. 8 is a top plan view illustrating a schematic configuration of another example of the microstructure plate.

A microstructure plate 90 illustrated in FIG. 9 comprises a substrate 92 and numerous metallic nanorods 94 disposed on the substrate 92.

The substrate 92 has substantially the same configuration as the substrate 82 described earlier, and therefore detailed description thereof will not be given here.

The metallic nanorods 94 are metallic nanoparticles each having dimensions permitting excitation of localized plasmons and each shaped like a rod having the minor axis and the major axis different in length from each other. The metallic nanorods 94 are secured so that they are fixedly disposed on one surface of the substrate 92. The minor axis of the metallic nanorods 94 measures about 3 nm to 50 nm, and the major axis measures about 25 nm to 1000 nm. The major axis is smaller than the wavelength of the excitation light. The metallic nanorods 94 may be formed of the same metal as the metallic particles described above. For details of the configuration of metallic nanorods, reference may be had, for example, to JP 2007-139612 A.

The microstructure plate 90 may be produced by the same method as described above for the microstructure plate 80.

The microstructure plate 90 having such a configuration also produces localized plasmons around the metallic nanorods and creates an enhanced electric field when the detection surface on which the metallic nanorods are disposed are irradiated by the excitation light.

Thus, also where the microstructure plate 90 having the above configuration is used, the microstructure plate can be likewise produced as when using the microstructure plate 12 and the microstructure plate 80 and, furthermore, the specimen can be detected with a high sensitivity.

Figure 9A:
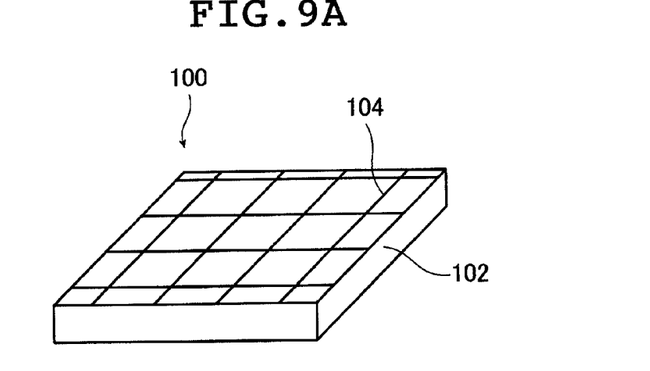
FIGS. 9A and 9B are a simplified perspective view and a sectional view showing a still further embodiment of a microstructure plate, respectively.
Figure 9B:
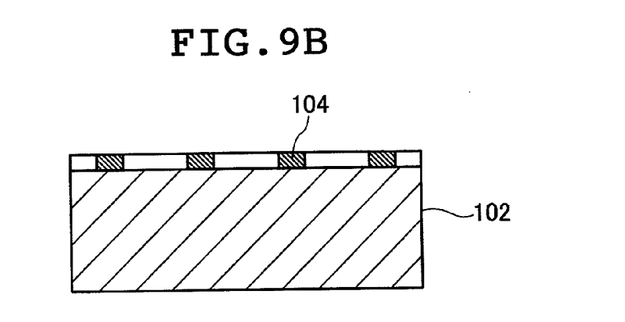

Now, reference is made to FIG. 9A, which is a perspective view illustrating a schematic configuration of another example of the microstructure plate; FIG. 9B is a sectional view of FIG. 9A.

A microstructure plate 100 illustrated in FIG. 9A comprises a substrate 102 and numerous thin metallic wires 104 provided on the substrate 102.

The substrate 102 has substantially the same configuration as the substrate 82 described earlier, and therefore detailed description thereof will not be given here.

The thin metallic wires 104 are linear members each having a line width permitting excitation of localized plasmons and arranged like a grid on one surface of the substrate 102. The thin metallic wires 104 may be formed of the same metal as the metallic particles and the metallic members described earlier. The thin metallic wires 104 may be produced by any of various methods used to produce metallic wiring including but not limited to vapor deposition and plating.

The line width of the thin metallic wires 104 is preferably not greater than a mean free path of electrons that oscillate in metal in response to light and specifically 50 nm or less, and preferably 30 nm or less. The thin metallic wires 104 may be arranged in any pattern including but not limited to a pattern where the thin metallic wires do not cross each other, i.e., are parallel to each other. The thin metallic wires 104 are also not limited in shape to straight lines and may be curved lines.

The microstructure plate 100 having such a configuration also produces localized plasmons around the thin metallic wires and creates an enhanced electric field when the detection surface on which the thin metallic wires are arranged is irradiated by the excitation light.

Thus, also when the microstructure plate 100 having the above configuration is used, the microstructure plate can be likewise produced as when using the microstructure plate 12, the microstructure plate 80, and the microstructure plate 90 and, furthermore, the specimen can be detected with a high sensitivity.

Further, the microstructure plate is not limited to the microstructure plate 12, the microstructure plate 80, the microstructure plate 90, or the microstructure plate 100; the microstructure plate may have a configuration comprising projections capable of exciting localized plasmons from each of these microstructure plates.

Further, where the metallic particles are formed by vapor-deposition on the substrate, the vapor deposition on the substrate may be effected from various directions.

Preferably, the microstructure plate is so constructed that the metallic particles are first disposed on the substrate, followed by vapor deposition of a metallic film on the substrate to form the projections. Thus, when the metallic film is vapor-deposited after the metallic particles are disposed, the metallic film can be formed between the metallic particles (fine metallic particles) so that the metallic particles and the metallic film can be placed in close contact, and thus the number of hot spots on the detection surface of the microstructure plate can be increased.

In the embodiments described above, a liquid sample is dropped onto the detection surface of the microstructure plate by a liquid sample dropping means. However, the invention is not limited in this regard. For example the liquid sample may be supplied to (i.e., brought into contact with) the detection surface of the microstructure plate by forming a flow channel for feeding the liquid sample to the surface of the microstructure plate and having the liquid sample flow through this channel.

Alternatively, instead of dissolving the analyte in a solvent to form a liquid sample, a method may be employed for attaching the analyte in an unmodified form on the detection surface of the microstructure plate.

Also, in the foregoing embodiments, to enable detection of the Raman signal from the analyte at a higher sensitivity, it is advantageous for the inventive method of measuring Raman signals to include also a background removing step in which background signals are removed from the analyte Raman signal normalized in the above-described normalization step.

The present invention enables the variability in signal intensity between microstructure plates to be further reduced without the need to use a reference substance for normalizing the Raman signal, and without having to take into account the affinity between the analyte and a reference substance. That is, the present invention enables the Raman signal from an analyte to be detected at a high sensitivity by using surface-enhanced Raman spectroscopy, and also enables the detection of a signal intensity proportional to the Raman signal from the analyte regardless of the strength of the enhanced electric field generated at the detection side of the microstructure plate.

As a result, it is possible to properly identify an analyte with high precision, and moreover to detect the amount and concentration of the analyte.

Moreover, because the Raman signals of the analyte can be detected to a high accuracy regardless of the strength of the enhanced electric field generated at the detection side of the microstructure plate, the tolerance for production errors can be increased, enabling a higher yield to be achieved and production costs to be reduced.

Although embodiments of an apparatus and method of measuring Raman signals according to the invention have been described in detail above for the purpose of illustration, those skilled in the art will appreciate that various modifications and variations are possible without departing from the scope and spirit of the invention.

EXAMPLES

The present invention is described more fully in the following example, which is illustrative and should not be construed as limiting the invention.

Twelve microstructure plates of the above-described construction shown in FIG. 2 were each furnished in turn as the microstructure plate 12.

Plate 1 was mounted, as the microstructure plate 12, at a given position in the Raman signal measuring apparatus 10 shown in FIG. 1, and secured in place.

Next, 100 µM of a liquid sample S was prepared by dissolving an analyte 60 (Rhodamine 6G, having a key band at 1360 cm$^{-1}$) in ethanol. This liquid sample S was added drop-wise onto the detection surface of Plate 1 using a dropper and dried, thereby causing the analyte 60 to adhere to the surface of the detection surface 12a.

Figure 10:
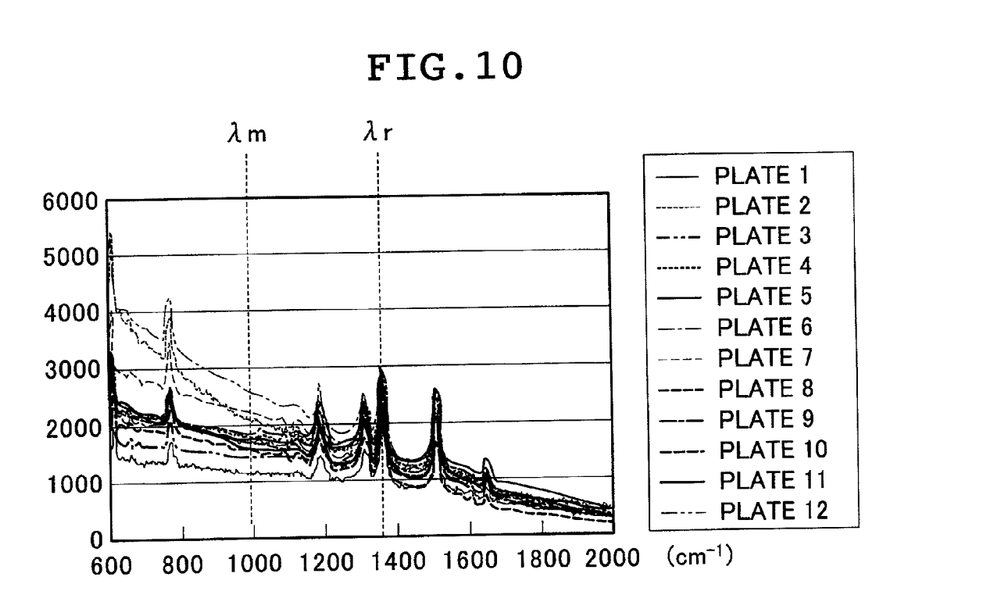
FIG. 10 is a graph showing the Raman signals from an analyte and the background signals detected in an Example.

Subsequently, the detection surface 12a was irradiated with a semiconductor laser having an output of 2 mW and an excitation wavelength of 785 nm, thereby generating an enhanced field on the detection surface 12a. An enhanced Raman signal from the analyte 60 and a background signal were detected with a Raman microspectrometer (manufactured by Horiba Jobin Yvon; LabLAM HR-800). The Raman signal from the analyte 60 and the background signal that were detected are shown in FIG. 10.

Next, a wavelength of 1000 cm$^{-1}$ was selected as the specific wavelength $\lambda_m$ because this differs from the wavelength $\lambda_r$ (1360 cm$^{-1}$) of the Raman signal from the analyte 60.

The Raman signal from the analyte 60 was then normalized by dividing the intensity of the Raman signal from the analyte 60 by the intensity of the background signal at the wavelength $\lambda_m$ (1000 cm$^{-1}$).

Plate 1 was replaced with Plate 2, and the same amount of liquid sample prepared as described above was added drop-wise to the detection surface of Plate 2 and dried, causing the analyte 60 to adhere to the surface of the detection surface 12a thereof. Next, a Raman signal from the analyte 60 and a background signal were detected in the same way as described above. The Raman signal from the analyte 60 was normalized by dividing the intensity of the Raman signal from the analyte 60 by the intensity of the background signal at the wavelength $\lambda_m$ (1000 cm$^{-1}$).

A normalized Raman signal for the analyte was similarly determined using each of Plates 3 to 12 in turn.

The Raman signals for the analyte 60 and the background signals that were detected using Plates 1 to 12 are shown in FIG. 10.

As shown in FIG. 10, the variability between microstructure plates in the intensity at the time of measurement (before normalization) was large, the coefficient of variation being 40%. By contrast, the variability between microstructure plates in the intensity following normalization decreased to a coefficient of variation of 20%. The coefficient of variation (CV) is a numerical indicator of the breadth of distribution (variance) of measured data; a small CV indicates a lower variability in the intensity.

In this way, by normalizing the Raman signal from an analyte using the intensity of a background signal at a specific wavelength, the intensity of Raman scattered light from the analyte can be detected to a high accuracy.

Moreover, by carrying out an assay based on the normalized intensity, the amount or concentration of the analyte can be determined to a high accuracy.

The above results clearly show the beneficial effects of the present invention.

What is claimed is:

1. A method of measuring Raman signals, comprising:
   an analyte placing step of placing an analyte on a detection surface of a microstructure plate which generates an enhanced electric field when irradiated with excitation light;
   an irradiating step of irradiating the detection surface with the excitation light so that the enhanced electric field is generated around the detection surface and Raman scattered light is emitted from the analyte and the detection surface to be enhanced by the generated enhanced electric field;
   a Raman signal obtaining step of detecting the enhanced Raman scattered light emitted from the analyte to obtain a Raman signal from the analyte having a wavelength and detecting the enhanced Raman scattered light emitted from the detection surface of the microstructure plate to obtain at least one background signal for use as a reference having at least one specific wavelength which differs from the wavelength of the Raman signal from the analyte;
   an intensity measuring step of measuring respective intensities of the Raman signal from the analyte and the at least one background signal from the detection surface of the microstructure plate; and
   a normalizing step of normalizing the Raman signal from the analyte by dividing the measured intensity of the Raman signal from the analyte by the measured intensity of the at least one background signal from the detection surface of the microstructure plate obtained as the reference.

2. The method of claim 1, wherein the background signal having a specific wavelength is obtained as the reference in the Raman signal obtaining step.

3. The method of claim 2, wherein the specific wavelength of the background signal obtained as the reference differs from a wavelength of the Raman signal from the analyte.

4. The method of claim 1, wherein:
   a plurality of background signals at specific wavelengths are obtained as references in the Raman signal obtaining step; and
   the Raman signal from the analyte is normalized by calculating a sum or mean of intensities of the plurality of background signals having the specific wavelengths and dividing the intensity of the Raman signal from the analyte by the calculated sum or mean in the normalizing step.

5. The method of claim 4, wherein each of the specific wavelengths of the plurality of background signals obtained as the references differs from the wavelength of the Raman signal from the analyte.

6. An apparatus for measuring Raman signals, comprising:
   a microstructure plate on which is formed a detection surface that generates an enhanced electric field when irradiated with excitation light, for placing an analyte on the detection surface;
   excitation light radiating means that irradiates the detection surface of the microstructure plate with the excitation light so that the enhanced electric field is generated around the detection surface and Raman scattered light is emitted from the analyte and the detection surface to be enhanced by the generated enhanced electric field;
   detection means that detects the enhanced Raman scattered light emitted from the analyte to obtain a Raman signal from the analyte having a wavelength, detects the enhanced Raman scattered light emitted from the detection surface of the microstructure plate to obtain at least one background signal for use as a reference having at least one specific wavelength which differs from the wavelength of the Raman signal from the analyte, and measures respective intensities of the Raman signal and the at least one background signal from the detection surface of the microstructure plate; and
   normalization processing means that normalizes the Raman signal from the analyte by dividing the measured intensity of the Raman signal from the analyte by the measured intensity of the at least one background signal from the detection surface of the microstructure plate obtained as the reference.

7. The apparatus of claim 6, wherein the detection means obtains the background signal having a specific wavelength as the reference.

8. The apparatus of claim 7, wherein the specific wavelength of the background signal obtained as the reference by the detection means differs from a wavelength of the Raman signal from the analyte.

9. The apparatus of claim 6, wherein:
   the detection means obtains, as references, a plurality of background signals at specific wavelengths; and
   the normalization processing means normalizes the Raman signal from the analyte by calculating a sum or mean of intensities of the plurality of background signals having the specific wavelengths obtained by the detection means and dividing the intensity of the Raman signal from the analyte by the calculated sum or mean.

10. The apparatus of claim 9, wherein each of the specific wavelengths of the plurality of background signals obtained as the references by the detection means differs from the wavelength of the Raman signal from the analyte.

* * * * *